United States Patent
Barnes

(10) Patent No.: US 7,205,427 B2
(45) Date of Patent: *Apr. 17, 2007

(54) CROSS-COUPLING SYNTHESIS OF ALKYL (DIALKYLPHENYL) INDENES

(75) Inventor: Hamlin H. Barnes, Fort Collins, CO (US)

(73) Assignee: Boulder Scientific Company, Mead, CO (US)

( * ) Notice: Subject to any disclaimer, the term of this patent is extended or adjusted under 35 U.S.C. 154(b) by 702 days.

This patent is subject to a terminal disclaimer.

(21) Appl. No.: 10/161,850

(22) Filed: Jun. 4, 2002

(65) Prior Publication Data

US 2004/0267072 A1 Dec. 30, 2004

(51) Int. Cl.
*C07F 7/08* (2006.01)
*C07F 17/00* (2006.01)

(52) U.S. Cl. .............. 556/489; 11/12; 11/28; 11/53; 11/465; 526/127; 526/160; 526/351

(58) Field of Classification Search ........... 556/489, 556/11, 12, 28, 53, 465; 526/127, 160, 351
See application file for complete search history.

(56) References Cited

U.S. PATENT DOCUMENTS

| | | | |
|---|---|---|---|
| 5,789,634 A | 8/1998 | Sullivan et al. |
| 6,291,699 B1 | 9/2001 | Birmingham et al. |
| 6,479,646 B1 | 11/2002 | Nakano et al. |

*Primary Examiner*—Tam M. Nguyen
(74) *Attorney, Agent, or Firm*—Aileen Law; A Law Firm, P.C.

(57) ABSTRACT

A cross-coupling synthesis of 2-alkyl-4-(2,6-dialkylphenyl) indenes is described. A 2-alkylidene is treated with a dialkylboronic acid in the presence of a catalyst. A feature of the invention is the use of a cross-coupling catalyst comprising palladium dichloride (1,5-cyclooctadiene) as a cross-coupling catalyst.

15 Claims, No Drawings

CROSS-COUPLING SYNTHESIS OF ALKYL (DIALKYLPHENYL) INDENES

FIELD OF THE INVENTION

This invention relates to the cross-coupling synthesis of alkyl (dialkylphenyl)indenes. More particularly, the invention relates to the cross-coupling synthesis of 2-alkyl-4-(2, 6-methylphenyl)indenes, wherein a palladium dichloride (cyclooctadiene) cross-coupling catalyst may be utilized.

BACKGROUND OF THE INVENTION

The palladium(0) cross-coupling of an aryl halide and an aryl boronic acid (Suzuki reaction) was first described in *Synthetic Communications* 11:513–519 (1981). Development and application of the reaction have been extensively reviewed. See *Acta Chemica Scandanavia* 47:221–230(1993); *Chemical Reviews* 95:2457–2483 (1995); *Advances in Metal-Organic Chemistry* 6:187–243 (1998).

Sterically hindered examples having three to four substituents ortho to the newly formed biaryl bond continue to be a considerable challenge. The use of aryl chlorides as substrates in the reaction offers three distinct advantages compared to the use of either aryl bromides or aryl triflates. First, the variety of aryl chlorides that are commercially available is much greater than for either the bromides or triflates. Second, use of aryl chlorides offers the greatest atom economy compared to either the bromides or triflates. Third, aryl chlorides are nearly always much cheaper than either the bromides or triflate. See Trost, "The Atom Economy—A Search for Synthetic Efficiency Science," 254: 1471–1477 (1991).

One significant challenge to the use of aryl chlorides is that the oxidative addition of Pd(0) to the arene-chloride bond is very slow compared to the addition across the arene-bromide bond. There are fewer than ten reported examples of the use of aryl chlorides in a sterically hindered Suzuki reaction.

There are two usual sources of Pd(0) for the Suzuki reaction. They are tetrakis-triphenylphosphine palladium and tris-dibenzylideneacetone palladium. Both reagents have the disadvantage of being very air sensitive and, hence, are difficult to handle. Palladium acetate is the only reported salt used in the Suzuki reaction that is air stable. A few papers briefly mention an attempt to use palladium chloride with only minor success because it is polymeric. Palladium chloride is a desirable source of Pd(0) because it is cheaper than palladium acetate.

Pursuant to this invention, an air stable monomer of palladium chloride, viz. palladium chloride cyclooctadiene, is utilized. The exemplified 2-methyl-4-(2,6-dimethylphenyl)indene is a sterically hindered compound. Its synthesis involves the use of an aryl chloride affording the greatest atom economy and lowest cost of material. This new, cheap, air stable source of Pd(0) is shown to be equal to palladium acetate in performance.

U.S. Pat. No. 5,789,634 describes the synthesis of 2-methyl-4-phenylindene by a coupling reaction of phenyl magnesium bromide and 2-methyl-4-chloroindene catalyzed by bis-(1,3-diphenylphosphinopropane) nickel dichloride in 80% isolated yield and in multi-kilogram quantities. However, due to steric hindrance, the analogous reaction as applied to 2-methyl-4-(2,6 dimethylphenyl)indene did not give the desired product. See U.S. Pat. No. 6,291,699 (Col. 7, line 44 to Col. 8, line 3, "Comparative Example 3").

Examples 1 and 2 of U.S. Pat. No. 6,291,699 illustrate the synthesis of 2-methyl-4-(2,6-dimethylphenyl)indene. The exemplified synthesis requires the use of the costly phosphine ligand 2-dicyclohexylphosphine-2-methyl biphenyl. See *J. Org. Chem.* 65:1158–1174 (2000) (ligand 5, p. 1160).

Old, et al., *J. Am. Chem. Soc.* 120:9722–9723 (1998) describes the use of a monophosphine "ligand 2" significantly expands the scope of palladium-catalyzed aryl chloride transformation. The reported formula of "ligand 2" is

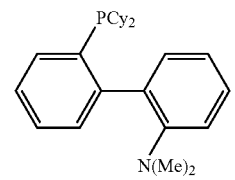

wherein $PCy_2$ means dicyclohexyl phosphine. According to Olds, supra, the "ligand 2" was prepared in three steps form N,N-dimethyl-2-bromoaniline.

This invention involves the unexpected discovery that the advantages attributed to "ligand 2" are substantially observed when the structural components of the ligand are concurrently utilized as separate methods in particular catalyzed aryl halide cross-coupling reactions.

DEFINITIONS

Cross-Coupling Reaction: Any reaction of an organometallic compound $\underline{R}$-$\underline{M}$ with an organic nucleophile $\underline{R^1}$—$\underline{X}$, wherein $\underline{R}$ and $\underline{R^1}$ are the same or different organic groups and $\underline{X}$ is a leaving group to give a product $R$—$R^1$.

SUMMARY OF THE INVENTION

This invention provides a cost effective, novel cross-coupling synthesis of 2-alkyl-4-(2,6-dialkylphenyl)indenes.

Pursuant to the invention, alkyl (dialkylphenyl) indenes are synthesized by reacting a haloindene with a dialkylphenylboronic acid in the presence of a cross-coupling catalyst. The haloindene ligand may have the formula

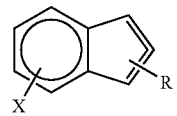

wherein X is any halogen, preferably chlorine, which may be substituted at any available position of the six-membered ring, and wherein R is hydrogen or an alkyl group, preferably a $C_1$ to $C_6$ alkyl group and which may be substituted at any available position of the five-membered ring. 2-methyl-4-chlorindene is preferred.

The dialkylphenylboronic acid may have the formula

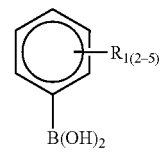

wherein $R_1$ is hydrogen or an alkyl group and the expression $R_{1(2-5)}$ means from 2 to 5 $R_1$ alkyl groups which may be substituted at any one or more positions on the six-membered ring. $C_1$ to $C_6$ alkyl groups are preferred. The preferred dialkylphenyl boronic acid is 2,6-dimethylphenyl boronic acid.

Any desired cross-coupling catalyst may be used. Appropriate catalysts are described in United States page U.S. Pat. No. 6,291,699 at Col. 2, line 60 to Col. 3, line 3. The preferred cross-coupling catalyst is palladium dichloride (1,5-cyclooctadiene) which may be written as ($PdCl_2$ (COD)). The preferred catalyst is easily prepared, undergoes facile reduction, and is air stable.

The synthesis reaction of the invention is generally illustrated by Equation 1:

EQUATION 1

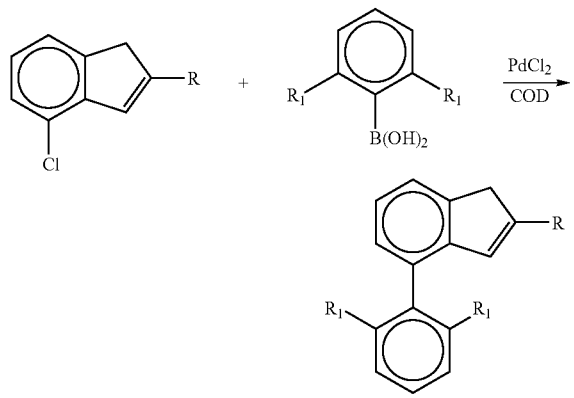

in which R and $R_1$ are as defined.

EXAMPLES 1 TO 7

In order to permit comparison of individual examples, the reactions were performed in the same solvent (200 mL toluene), were refluxed for the same time (12 hours), used the same molar concentration of palladium compound as catalyst (1 mol %), the same molar concentration of potassium phosphate (2.25 equivalents), and the same molar concentration of 2,6-dimethylphenylboronic acid (1.5 equivalents).

Experimental Method

A 500 mL three-neck flask is equipped for mechanical agitation and reflux, dried, and flushed with nitrogen. To the flask is added, in the following order: 225 mg palladium acetate (1 mol %); 1.18 g 2-(dimethylamino)-2'-(dicyclohexylphosphino) biphenyl (3 mol %); 22.5 g 2,6-dimethylphenyl boronic acid (1.5 mol equivalents); 16.5 g 2-methyl-4-chloroindene (0.1 mol, limiting reagent); 47.75 g potassium phosphate (2.25 mol equivalents); 200 mL toluene.

Begin agitation, and slowly heat the reaction over two hours to reflux (95C). Continue refluxing for 12 hours, after which time the reaction mixture is filtered hot. Wash the filter cake with 50 mL hot toluene. Combine the organic filtrates, and wash with 150 mL 10% HCl (aqueous), and then with 100 mL water, discarding the aqueous layer after each separation. Dry the organic solution over sodium sulfate. Distill the solvent and unreacted 2-methyl-4-chloroindene under high vacuum to a pot temperature of 90–100C. The product is crystallized from pentane at −10C, collected by filtration, and dried under high vacuum, yielding a white solid.

Results

The results are summarized in the table presented below:

| Example Number | Palladium Ligand | Phosphine Ligand | Ligand Mole % | % Isolated Yield |
|---|---|---|---|---|
| 1 | Pd(OAc)$_2$ | A | 3 | 88 |
| 2 | PdCl$_2$.COD | A | 3 | 86 |
| 3 | PdCl$_2$.COD | B&C | 3 | 74 |
| 4 | PdCl$_2$.COD | B&C | 4 | 81 |
| 5 | PdCl$_2$.COD | B&C | 8 | 78 |
| 6 | PdCl$_2$.COD | B | 3 | 34 |
| 7 | PdCl$_2$.COD | C | 3 | <2 |

Abbreviations used in the table:
Pd(OAc)$_2$: Palladium acetate
PdCl$_2$.COD: Palladium dichloride (1,5=cyclooctadiene)
A: 2-(Dimethylamino)-2'-(dicyclohexylphosphino)biphenyl
B: Phenyldicyclohexylphosphine
C: N,N-Dimethylaniline Reaction

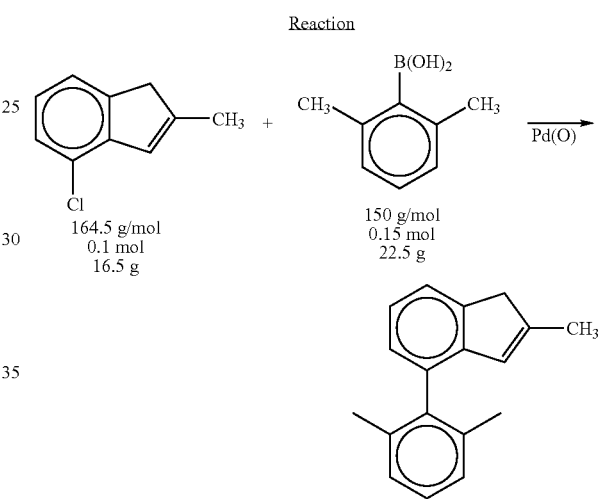

Method

1. A 500 mL 3-neck flask is equipped for reflux. Purge thoroughly with $N_2$. Add reagents in the following order:

| 286 mg | PdCl$_2$.COD |
| 1182 mg | 2-dicyclohexyl-2'-(N,N-dimethylamino)-2' biphenylphosphine |
| 22.5 g | 2,6-dimethylphenyl boronic acid |
| 16.5 g | 2-methyl-4-chloroindene |
| 46.7 g | K$_3$PO$_4$ |
| 225 ml | toluene |

2. Heat over 2 hours to reflux. Reflux reaction for 12 hours.

3. Filter the reaction, hot. Wash the filter with 2×45 ml hot toluene. Combine all filtrate.

4. Wash the toluene filtrate with 2×100 ml 10% HCl. Wash with water until neutral to pH paper. Dry over Na$_2$SO$_4$.

5. Distill all solvents under reduced pressure to a pot temperature of 50° C. Distill residual chloromethylindene under high vacuum and short path to a pot temperature of 100° C. Recrystallize the product in pentane at −10° C. Dry the off-white colored solid product under high vacuum. Yield=85%.

I claim:

1. A method for the synthesis of an alkyl(dialkylphenyl) indene which comprises treating a 2-alkyl haloindene with a dialkylboronic acid in a non-interfering solvent in presence of a cross-coupling catalyst.

2. The method of claim 1, wherein said cross-coupling catalyst comprises palladium dichloride cyclooctadiene.

3. The method of claim 1, wherein said non-interfering solvent is a hydrocarbon.

4. The method of claim 1, wherein said 2-alkyl haloindene is 2-alkyl-4-chloroindene.

5. The method of claim 1, wherein said dialkylboronic acid is a 2,6-dialkylphenyl boronic acid.

6. A method for synthesizing a 2-alkyl-4-(2,6-dialkyiphenyl) indene which comprises treating 2-alkyl-4-halo indene with a 2,6-dialkylboronic acid in the presence of a cross-coupling catalyst in a non-interfering hydrocarbon solvent.

7. The method of claim 6, wherein said cross-coupling catalyst comprises palladium dichloride and 1,5-dicyclooctadiene.

8. The method of claim 1, wherein said treating is conducted in a reflux temperature.

9. The method of claim 6, wherein the mole ratio of said 2-alkyl-4-halo indene to said 2,6-dialkylboronic acid is from about 1:1.3 to about 1:1.75.

10. The method of claim 6, wherein said 2-alkyl-4-halo indene is 2-methyl-4-chloro indene.

11. The method of claim 6, wherein said 2,6-dialkylboronic acid is 2,6-dimethylboronic acid.

12. The method of claim 2, wherein said non-interfering solvent is a hydrocarbon.

13. The method of claim 2, wherein said 2-alkyl haloindene is 2-alkyl-4-chloroindene.

14. The method of claim 2, wherein said dialkylboronic acid is a 2,6-dialkylphenyl boronic acid.

15. The method of claim 6, wherein said treating is conducted in a reflux temperature.

* * * * *